United States Patent
Stevenson et al.

(10) Patent No.: US 6,750,756 B2
(45) Date of Patent: Jun. 15, 2004

(54) USE OF ISOTOPES TO PROVIDE INFORMATION TO AN ARTICLE

(75) Inventors: Nigel R. Stevenson, Sugar Hill, GA (US); John M. Dawson, deceased, late of Walnut Creek, CA (US), by Margaret Obendorf (executrix); Lee Heflinger, Torrance, CA (US)

(73) Assignee: Theragenics Corporation, Buford, GA (US)

( * ) Notice: Subject to any disclaimer, the term of this patent is extended or adjusted under 35 U.S.C. 154(b) by 0 days.

(21) Appl. No.: 10/213,917

(22) Filed: Aug. 7, 2002

(65) Prior Publication Data

US 2003/0030558 A1 Feb. 13, 2003

Related U.S. Application Data

(60) Provisional application No. 60/310,975, filed on Aug. 8, 2001.

(51) Int. Cl.[7] ............................................... G08B 13/14
(52) U.S. Cl. ................. 340/5.86; 340/5.8; 340/572.1; 340/572.4; 252/408.1; 252/625; 324/300; 324/307
(58) Field of Search ................. 340/5.86, 5.8, 340/572.1, 572.3, 572.4; 250/302, 303; 378/45, 47, 53; 436/56; 324/300, 307; 252/408.1, 625

(56) References Cited

U.S. PATENT DOCUMENTS

| | | | |
|---|---|---|---|
| 4,507,349 A | 3/1985 | Fromson et al. | |
| 4,742,340 A | 5/1988 | Nowik et al. | |
| 4,862,143 A | 8/1989 | Hirshfield et al. | |
| 5,324,567 A | 6/1994 | Bratchley et al. | |
| 5,718,754 A | 2/1998 | Macpherson et al. | |
| 5,760,394 A | 6/1998 | Welle | 250/303 |
| 5,826,507 A | 10/1998 | Lim | |
| 5,853,464 A | 12/1998 | Macpherson et al. | |
| 5,935,755 A | 8/1999 | Kazmaier et al. | |
| 5,966,205 A | 10/1999 | Jung et al. | |
| 5,986,550 A * | 11/1999 | Rapaport et al. | 340/572.3 |
| 6,008,888 A | 12/1999 | Nottke et al. | |
| 6,038,016 A | 3/2000 | Jung et al. | |
| 6,218,943 B1 * | 4/2001 | Ellenbogen | 340/572.4 |
| 6,477,227 B1 | 11/2002 | Kaiser et al. | 378/45 |

* cited by examiner

Primary Examiner—Michael Horabik
Assistant Examiner—Yves Dalencourt
(74) Attorney, Agent, or Firm—Knoble & Yoshida LLC (57) ABSTRACT

A method for associating information with an article, an isotopic labeling composition to label an article with information using at least two different isotopes of an element, and an article labeled with the labeling composition. In the labeling composition, the isotopes of the labeling composition have an abundance ratio that is detectably different from the natural abundance ratio thereof. By detecting the abundance ratio(s) of the isotopes in the labeling composition, via laser ablation/magnetic spectroscopy, an NQR spectrometer, an NMR spectrometer, an IR spectrometer, or a microwave spectrometer, information about the article can be determined. The method and labeling composition may be used to identify, authenticate or determine the source or origin of an article or to provide detailed information about an article.

37 Claims, 10 Drawing Sheets

USE OF ISOTOPES TO PROVIDE INFORMATION TO AN ARTICLE

CROSS-REFERENCE TO RELATED APPLICATIONS

This application claims the benefit under 35 U.S.C. §119 (e) of U.S. provisional application No. 60/310,975, filed on Aug. 8, 2001.

BACKGROUND OF THE INVENTION

A. Field of Invention

The invention relates to the use of isotopes to provide information to an article.

B. Description of the Prior Art

As a result of technology advances in reproduction techniques, many articles have become vulnerable to counterfeiting. This problem is particularly acute for items such as credit cards, compact discs, certificates, passports, identification cards, designer fashion accessories and clothing. In addition, an even more serious problem is the counterfeiting of currency, bank notes and other financial paper. A related problem is the unauthorized use of a financial item, such as a credit card, a registered security or an identity document.

Many techniques have been developed for labeling articles to prevent counterfeiting or fraudulent use. Techniques such as holograms on credit cards and magnetic coding on various articles have been in use for some time. These prior art techniques have been less than fully effective either because the counterfeiters have found ways to duplicate the label, or the apparatus for detecting the label and verifying its authenticity has been too expensive or cumbersome to be accepted for widespread use.

U.S. Pat. Nos. 4,742,340 and 4,862,143 teach the use of a γ-ray radiation technique to detect counterfeit articles by labeling the articles with an enriched isotope such as iron-57, tin-119 or europium-151. However, this method requires a γ-ray source and γ-ray detector, which are perceived to be too hazardous for general use.

It is an object of certain embodiments of the present invention to provide a labeling composition for associating information with an article, which cannot be easily duplicated.

It is also an object of certain embodiments of the present invention to provide a method to obtain information about an article, which is fast, inexpensive and simple, yet provides a high level of security against fraud, counterfeiting or duplication.

It is also an object of certain embodiments of the present invention to provide an article including a label which can be easily read to provide information about the article, yet provides a high level of security against counterfeiting, fraud or duplication.

These and other objects of the invention will be apparent from the summary and detailed description, which follow.

SUMMARY OF THE INVENTION

In a first aspect, the present invention provides a composition for labeling an article that includes at least two isotopes of the same element at a predetermined abundance ratio.

In a second aspect, the present invention relates to a method for labeling an article with at least two isotopes of the same element and detecting the abundances and/or abundance ratio of the at least two isotopes of the same element to obtain information about the article.

In a third aspect, the present invention relates to an article labeled with at least two isotopes of the same element to thereby associate information about the article with the article by virtue of the isotope-containing label.

DETAILED DESCRIPTION OF THE PREFERRED EMBODIMENTS

In a first aspect, the present invention relates to an isotopic labeling composition for labeling an article for associating information with the article. The composition contains a predetermined amount of two or more isotopes of at least one element.

Suitable chemical elements for use in the present invention exist in the form of two or more isotopes. Each isotope of a particular element typically exists in nature in a particular, known abundance relative to other isotopes of the same element. This so-called natural abundance of each particular isotope is a well-defined constant. Nearly all materials used to manufacture goods are used in a form that has the same relative abundances of the various isotopes as occurs in nature. The natural abundances of various isotopes can be found in most physical chemistry handbooks.

The present invention is based on the concept that by artificially changing the relative abundances of one or more isotopes of a particular chemical element, a unique label based on the particular composition can be created for use in labeling articles with information about the article.

The relative abundances of isotopes of a chemical element in a particular material or composition can be altered by several different methods. One method involves enriching the material with one or more isotopes. A second method involves extracting one or more isotopes from the material to thereby alter the relative abundances of the different isotopes contained in the material. The isotopes may be used in elemental form, in the form of a chemical compound or mixtures thereof.

A specific isotope of a composition can be prepared or isolated by using conventional methods of extracting isotopes. Conventional methods for extracting isotopes include plasma separation processes (PSP), electromagnetic separation, molecular laser isotope separation (MLIS), atomic vapor laser isotope separation (AVLIS), gas centrifugation, gas diffusion and distillation. All of these methods are well known to persons skilled in the art. The preferred method to prepare the isotopes for use in the present invention is PSP due to the quantities of isotopes that may be required for this application.

Although these methods of altering isotope ratios are widely known, each of them require specialized equipment that is not easily available to counterfeiters. This provides a high degree of security against counterfeiting the label. It should be noted that chemical processing does not significantly alter isotope ratios.

Any chemical element having two or more isotopes can be employed in the present invention. The preferred element should display a good sensitivity towards the particular detection method employed. For example, when NMR spectroscopy (hereafter "NMR") is used as the means for detecting the isotopes, the relaxation times T1 and T2 of the isotopes, among many other factors, have to be considered in order to select a suitable labeling composition. The isotopes to be detected by NMR should also have spins equal to or greater than ½. When "zero-field NMR," also called nuclear quadrupole resonance spectroscopy (hereafter "NQR'), is used to detect the abundances and/or abundance ratio of the isotopes in the composition, the isotopes being detected should have spins greater than ½. Methods of detecting isotopes using NQR are known to a skilled person in the art. See Abragan, The Principles of Nuclear Magnetism, Oxford, 1961, pages 16 and 249; Methods of Experimental Physics, Vol. 3, Molecular Physics, Dudley Williams ed., Academic Press, 1962, pages 501–524; and Clark, Pulsed Nuclear Resonance Apparatus, Review of Scientific Instruments, Vol. 35, No. 3, March 1964, pages 316–333, all of which are incorporated by reference herein for their disclosures of NQR detection methods and apparatus. "Spin" used herein is a quantum parameter of the nuclei of an isotope. For a particular isotope, the spin is generally a known value which can be found in a handbook.

The isotopes used in the present invention may be incorporated in the composition of the invention in a metallic form or as an element of one or more compounds. Exemplary elements and compounds that can be incorporated in the composition of the invention are Re, $ReBr_3$, $ReO_2$, $ReS_2$, Cu, $CuF_2$, $Cu(NO_3)_2$, $3H_2O$, CuO, $Cu_2O$ $Cu_2S$, CuS, Rb, $Rb_2CO_3$, RbF, $RbNO_3$, $Rb_2SO_4$, Sb, $Sb_2O_5$, $Sb_2O_3$, $SbCl_3$, $SbF_3$, Eu, $Eu_2O_3$, $EuCl_3$, $EuF_3$, $EuBr_3$, In, $InF_3$, $InCl_3$, $InBr_3$, $C_6H_4Cl_2$ and $C_6H_4Br_2$.

Alternatively, the isotopes used in the present invention may be employed in the form of alloys, powdered metals or eutectic compounds. Such alloys, powdered metals or eutectic compounds can include two or more isotopes of a single element and/or two or more elements. At least one element in an alloy, powdered metal or eutectic compound is present in the form of two or more isotopes, although it is also possible to employ two or more isotopes of each of two or more different elements, particularly if it is desirable to increase the quantity of information contained in the label. This embodiment may be employed to provide a more complex signature by combining several isotopes and elements into a single composition to thereby increase the number of isotopic ratios that can be employed to provide information.

When NMR or NQR is used as a preferred detection method, the composition of the present invention that is used to label an article preferably comprises an isotope-containing compound or material that has the following characteristics:

1. The compound is suitable for isotope ratio modification using one of the above-mentioned methods or other suitable methods;
2. At least one element of the compound preferably has at least two isotopes that are present in sufficient quantities to provide a detectable signal;
3. The isotopes of the element in the compound should preferably have high NMR or NQR resonant frequencies;
4. The compound should preferably produce NMR or NQR signals with narrow line widths;
5. The compound preferably contains a relatively large amount of the element to be detected;
6. The compound is preferably used in one form of crystalline structure instead of being a mixture of multiple crystalline forms to avoid multiple resonance frequencies and avoid unnecessary reduction of signal strength;
7. The compound should preferably be relatively stable (e.g., not prone to oxidation, or hydrolysis); and
8. The compound should preferably be substantially non-toxic to the users of the labeled article and/or detection equipment.

In one preferred embodiment, when NQR is used as the preferred detection method, the most preferred element for use in the composition of the present invention is selected from the group consisting of bromine, chlorine, copper and antimony. Compounds of bromine, chlorine, copper and antimony can also be used in the compositions of the present invention. For example, $Cu_2O$ (having an NQR frequency of 20.337 MHz and a line width of 20 KHz), CuO, CuS (having NQR frequencies of 13.7 and 14.7 MHz, and line widths of 50 KHz), $Cu_2S$, antimony metal powder (having NQR frequencies of 21.506 and 19.580 MHz and line widths about 10 KHz at room temperature), $Sb_2O_3$ (such as antimony ores Senarmontite or Valentinite), paradichlorobenzene, and paradibromobenzene can be used in the composition of the present invention. These compounds and/or metals can be used alone, with a carrier, or encapsulated in a substantially inert material. The carrier used in the composition may be any inert material to facilitate the composition being incorporated into an article to be labeled. An inert material is a material that does not react with the compound containing the isotopes. In addition, the carrier is preferably a material that does not contribute to or interfere with the signal of the isotopes being detected and does not adversely affect the detection of the isotope abundance and/or abundance ratios, other than the normal effect of diluting the isotopes with an inert material. The carrier may be homogeneously or heterogeneously mixed with the element or compound, or be in contact with the element or compound. Preferably, the carrier used for an NQR detection method is a solid. For example, a compound containing the desired isotopes may be mixed or in contact with an adhesive material to form the composition of the present invention to facilitate the incorporation of the composition into an article being labeled.

The isotopic label should be incorporated into the object labeled in such a way that counterfeiters cannot easily remove the label and insert the removed label into other counterfeit objects.

In another embodiment, when an NMR spectrometer is used to detect the isotope abundances or abundance ratios, the preferred elements for use in the compositions of the present invention include tin, antimony and indium. The most preferred elements for use in the compositions of the present invention include tin and indium. Tin and indium may offer several advantages when NMR is used as the preferred detection method. First, isotopes of these elements are difficult to manufacture (in large enough quantities) except via PSP, which is a process that can only be performed at a few locations that have suitable equipment and experience. This provides a high degree of security since the isotopes needed for the labeling composition will be difficult to manufacture or obtain and the high startup cost of building and operating a PSP will serve to further deter would be counterfeiters. Further, certain isotopes of these elements provide excellent detection signals in the environments in which they are to be employed. This can be used to ensure the accuracy of the detection method, simplify the detection apparatus and permit a greater number of possible isotope combinations for use as labeling compositions. Another advantage of tin, and indium is that these isotopes are non-toxic in the environment in which they will be used and at the levels required to provide a suitable labeling composition. Furthermore, normal chemical and physical tests cannot be used to distinguish among certain isotopes of these materials making it even harder to duplicate these labeling compositions. The preferred isotopes for use in compositions of the present invention for use with NMR detection include tin-115, tin-117, tin-119, indium-113, and indium-115.

When NMR is used as the preferred detecting method, the isotopic labeling composition may also include a suitable carrier. The carrier used in the present invention is preferably a material that can disperse or dissolve one or more isotopes. The carrier used in the composition may be any inert material (a material does not react with the compound containing the isotopes) to facilitate the composition being incorporated into an article to be labeled. In addition, the carrier should not adversely affect the detection of the isotopes in the composition. The carrier may be a solid with a micro-structural mobility, which dissolves one or more isotopes to provide a substantially homogenous product. Alternatively, the carrier is a liquid, which dissolves one or more of the isotopes to provide a substantially homogeneous solution. Suitable liquids include solvents, water and alcohols. It is preferred to use two isotopes in a homogeneous mixture since such a mixture is more difficult to counterfeit.

The solid with a micro-structural mobility may include plastics, rubbers, oils, waxes and mixtures thereof. Preferably the solid is natural or synthetic rubber. Persons skilled in the art know the concept of micro-structural mobility as applied to at least plastics and rubber. Micro-structural mobility is desirable in the labeling compositions of the present invention because micro-structural mobility provides NMR measurements with narrower line widths, which are more consistently indicative of the true isotopic abundances in the article than would be NMR measurements of a simple solid. This provides a higher degree of accuracy in measurements using the labeling compositions of the invention with the associated advantages as discussed above.

When NMR is used to measure the abundances and/or abundance ratios of the isotopes in the labeling compositions, carriers allowing micro-structural mobility may improve the detectability of the isotopes. The isotopes used in the labeling compositions of the invention may preferably be dissolved in a liquid such as a solvent when the isotopes are in soluble forms such as $InCl_3$. Alternatively, an isotope is retained or captured in a clathrate to achieve a good mobility. Clathrates are molecules with hollow spaces in which other atoms can be trapped. Therefore, isotopes trapped in clathrates may provide narrow easily detectable resonance when they are detected using a detector such as an NMR instrument. Furthermore, an isotope can be retained or captured in a bulkyball to achieve a good mobility. A bulkyball is a well-known, hollow, giant molecule comprising mainly carbon. For example, one type of bulkyball is $C_{60}$.

Other methods can also be used to detect isotope abundances and/or abundance ratios in the labeling composition of the invention. These methods include, for example, laser ablation/magnetic spectroscopy, infrared (hereafter "IR") spectroscopy, and microwave spectroscopy using a laser ablation/magnetic spectrometer, an IR spectrometer and a microwave spectrometer, respectively.

There are a variety of methods for associating information to an article using the isotopic composition in accordance with the present invention. One method involves providing an amount of a particular isotope in the composition, which amount is different from the amount of that isotope which would be present in the composition in its natural abundance. The enrichment or depletion of one or more of a plurality of isotopes of a particular element in a composition to thereby alter the relative abundances of the isotopes from their natural abundances can be employed to provide a unique composition for providing information about an article. In addition, bar coding may be constructed based on patches of at least two different compositions having different ratios of isotope abundances.

In a preferred embodiment, the labeling composition contains isotopes that have abundances and/or abundance ratio(s) that are detectably different from the natural abundances and/or abundance ratio(s) of the respective isotopes. "Detectably different" abundances and/or abundance ratios means the difference between the first abundances and/or abundance ratios of a labeling composition of the invention and the respective second abundances and/or abundance ratios being detected is larger than the experimental error of a particular detection method that is capable of detecting the isotope abundances and/or abundance ratios in the labeling composition.

In another embodiment of the invention, specific ratios of two or more isotopes of a particular element can be employed to provide unique labeling compositions, which can be used to provide information about an article. It is also possible to use ratios of isotopes of two or more elements to provide additional variations in the compositions, which can be used or to provide additional information about the article or a higher level of security by making such compositions even more difficult to duplicate.

The article to be identified or authenticated is typically an important or valuable item. For example, the article may be a banknote, currency, a credit card, an identification card, a passport, a ticket, a certificate, etc. Alternatively, the article may be anything for which the association of information with the article is important, for example, luxury goods, designer goods, currencies, charge cards, debit cards, identification documents, passports, licenses, negotiable instruments, tickets, collector's items, precious metals, jewels, art works, rare goods, ingestible products, stock certificates, medical devices and similar products.

The ratio between the amount of the one or more isotopes and the amount of carrier can vary greatly depending on the nature of the carrier and the isotopes. Other factors, such as the cost of the isotope, the nature of the article to be labeled, the intended detection technique and the sensitivity of the detection technique, may affect the selection of the ratio of carrier to isotopes. A person skilled in the art can determine the appropriate ratio for a particular application.

To associate certain information with a particular article and/or authenticate a particular article, an article in accordance with the present invention may be labeled with a labeling composition of the present invention. The article can be labeled with the isotope composition of the present invention in a variety of different ways. For example, a labeling composition can be printed on the surface of the article, embedded inside the article, or dispersed in the article. The labeling composition can be located throughout the article or located in a selected portion of the article.

Suitable printing processes for labeling an article with the isotopic labeling composition of the present invention are known to persons skilled in the art. In this embodiment, the isotopic labeling composition can be dispersed or dissolved in a printing ink or a suitable carrier for printing the composition onto the surface of an article. In this manner, the isotopic labeling composition can be included in the inks used to print currency, bank notes, and other important documents.

The isotopic labeling composition may also be embedded into an article. This can be accomplished by mixing the labeling composition with the article, encapsulating the labeling composition and impregnating the capsules into the article. Such capsules are preferably sufficiently strong to survive normal use and handling of the article, in order to prevent the isotopes from being separated from the labeled article or from migrating to other locations in the article to thereby upset the distribution of the isotopes in the labeling composition.

In a particular embodiment, when an NMR spectrometer is used as the detection apparatus, the isotopic labeling composition can be impregnated into the article directly in the form of solid particles, solid strands or liquid droplets. Preferably, such an impregnation process locates the isotopic labeling composition in a material having micro-structural mobility as discussed above. Thus, the isotopes can be dispersed in solid particles or strands of a material such as rubber, which has micro-structural mobility.

Generally, it is preferable to spread the labeling composition over the entire article if possible or practical to make the counterfeiting even more difficult. However, in some situations or out of practicality, it may be sufficient to label only a small section of the article with the labeling composition in order to save costs and simplify the labeling and detection processes. The remaining portion of the article need not be labeled.

If it is desirable to identify the source or origin of the article, a measurement of the ratio of the concentrations of two different isotopes can be taken and cross-referenced against a key, which indicates the source or origin of the composition based on the ratio of the isotopes. If desirable, this can be used as a check in addition to a printed indication of source or origin on the article to prevent counterfeiting of valuable or rare goods. Other information about the goods can be provided by the isotopic labeling composition by, for example, encoding a message in the article, or encoding a personal identification.

To provide additional security or to increase the number of possible labeling compositions, a combination of three or more isotopes can be employed. Using three isotopes, it is possible to generate two independently different abundance ratios that can be employed for conveying detailed information about the labeled article. Using four isotopes, it is possible to generate three independently different ratios that can be employed for conveying information about the labeled article. It is also possible to combine different combinations of at least two isotopes from at least two different elements in one labeling composition to convey even more information.

In an alternative embodiment, a combination of two different isotopes can be employed using two or more different labels having different ratios of the two isotopes. In this manner a type of bar coding effect can be achieved with each bar being made up of a different combination of the two different isotopes in a particular ratio relative to one another, respectively. This provides a means for conveying large amounts of information about the labeled article or for generating a large number of unique identifiers using only two different isotopes.

An isotopic label may comprise one or more isotopes, which may be arranged in a suitable pattern to incorporate information about the article. The label can be identified by one or both of its pattern and its isotopic composition. A suitable pattern may be achieved by, for example, embedding the labeling composition in the article in a predetermined pattern or by printing the labeling composition on a surface of the article. The printing and embedding processes used for provision of the label are as described above. Exemplary patterns include, but are not limited to, bar codes, graphs, numbers, symbols and randomized arrays of dots, lines, shapes, etc.

The label can be either visible or invisible to the human eye. The isotope composition information contained in the label can be detected by the methods described above using the apparatus described below. The information encoded in the pattern of the label can be retrieved by scanning, imaging or other appropriate methods using one of the detection methods described above. The retrieved information can be processed by a computer to identify the article or authenticate the article using a database, well known algorithms, predetermined coding schemes or the like.

The isotope abundances and/or abundance ratios in the composition may be measured using any suitable apparatus, which is capable of providing information regarding the relative abundance of at least two different isotopes of the same chemical element present in the composition. In a simple embodiment, if the measured abundance of at least one isotope matches a predetermined level, this can be used to determine specific information about the article or the article can be authenticated or identified.

The isotope detection apparatus useful in the present invention typically employs a non-ionizing radiation source, which emits a radiation which does not chemically alter the isotopes being detected, and a detector, which can detect an output signal. The output signal results from the radiation interacting with one or more isotopes in the isotopic labeling composition. Suitable detection apparatus include, but are not limited to, a laser ablation/magnetic spectrometer, an infrared spectrometer, a microwave spectrometer, and NQR spectrometer and an NMR spectrometer.

Figures 1, 2:
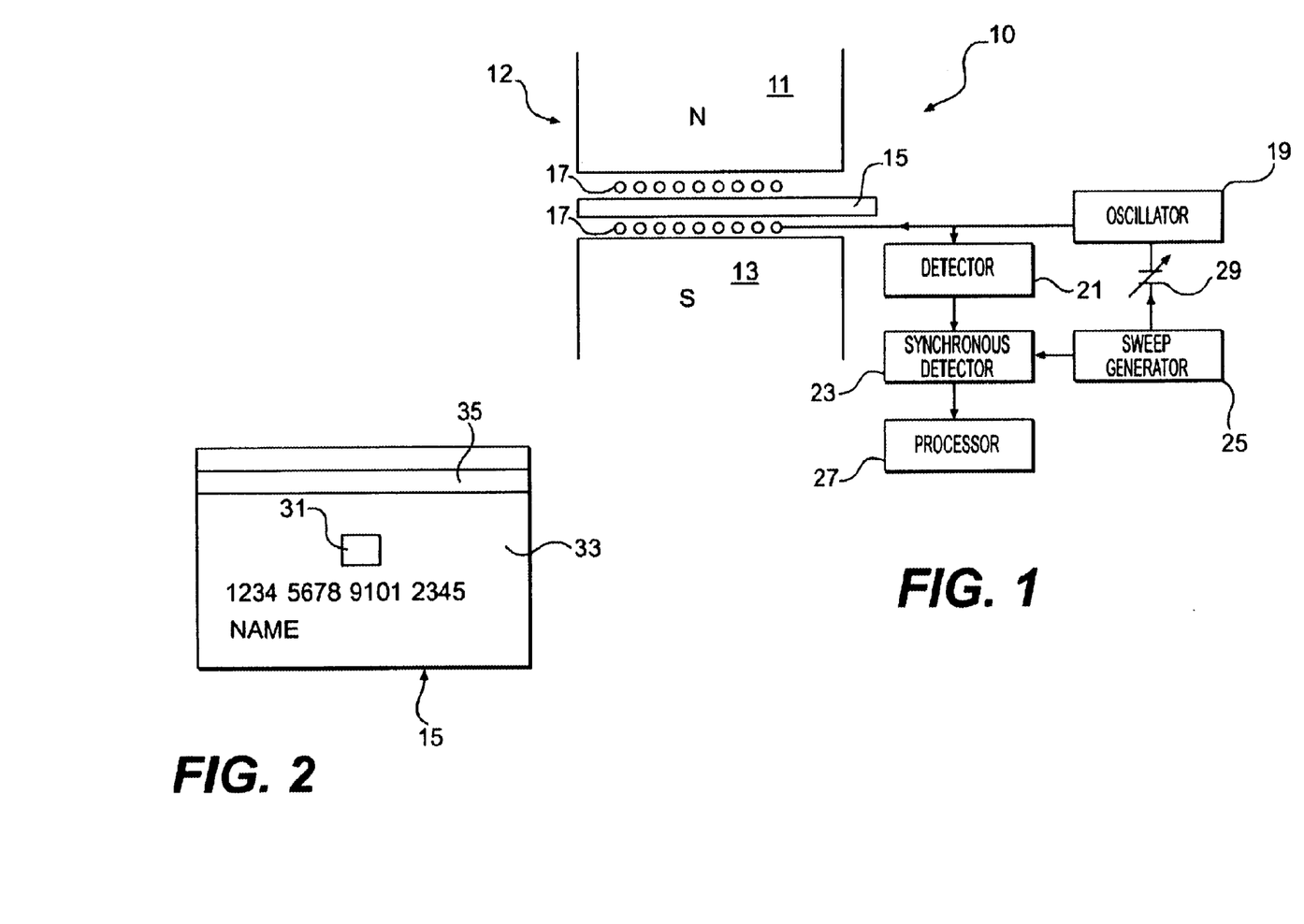
FIG. 1 is a schematic view of an NMR spectrometer that is suitable for identifying or authenticating articles according to the present invention.
FIG. 2 shows a credit card labeled with an isotopic labeling composition in accordance with the present invention.

An embodiment of a suitable apparatus for use in determining isotopic abundances is depicted in the drawing. An NMR spectrometer 10 for suitable for use as a detection apparatus in the method of the present invention is illustrated in FIG. 1. Magnet 12 creates a magnetic field between its north pole 11 and south pole 13. One or more excitation coils 17 are located in the magnetic field. Article 15 is placed in the spectrometer 10 as shown. Oscillator 19 sends a pulse to excitation coil 17, which then excites the nuclei of the isotopes of the labeling composition in article 15 to their excited states. After the pulse, the nuclei return to a lower energy state and emit a signal, which is detected by excitation coil 17 and sent to a detector 21. The output from detector 21 is then sent to synchronous detector 23. This process of excitation and relaxation of the nuclei is controlled by a sweep generator 25, which controls synchronous detector 23 and also controls oscillator 19 via a frequency varying device 29. Synchronous detector 23 measures the isotope abundances in the labeling composition and optionally determines if the measured result is consistent with a predetermined labeling composition for a genuine article. The result of the determination is sent to a processor 27 to provide information about the article. In order to optimize the NMR spectrometer 10, a number of factors, such as T1 and T2 of the isotopes, number of isotope nuclei per unit volume, magnetic field strength and uniformity, the drive electronics and its pulse sequence and amplitude, the data acquisition time and processing, the coil configuration and sample handling arrangement, the robustness or error rate of the accept-reject decision process, and cost of production machines, etc, have to be considered. The NMR spectrometer is advantageous in measuring certain isotope abundances and/or abundance ratio(s), because it provides a favorable signal-to-noise ratio, especially when the labeling composition is in liquid form. If the labeling composition is a solid at room temperature, the labeling composition can be heated to an elevated temperature to enhance microstructural mobility and thereby improve the signal-to-noise ratio. Most commercial NMR spectrometers include their own heating and cooling systems for this purpose. Alternatively, an NMR spectrometer with a solid-state probe can be used to detect isotope concentrations in solid labeling compositions. The solid-state probe typically involves using a magic angle spinning apparatus during the taking of the measurement.

An article 15 labeled in accordance with the present invention is shown in FIG. 2. Section 31 of labeled article 15 preferably contains the isotopic labeling composition. Section 33 of labeled article 15 need not contain any isotope composition or it may contain a reference composition. The article 15 may contain a reference composition, which makes up section 33 of labeled article 15 that can be used to establish the baseline for a particular measurement apparatus. Preferably, a reference composition including the isotopes in the naturally occurring abundance ratio is employed. The article 15 may also contain information on a magnetic strip 35 or in any other suitable form.

Figure 3:
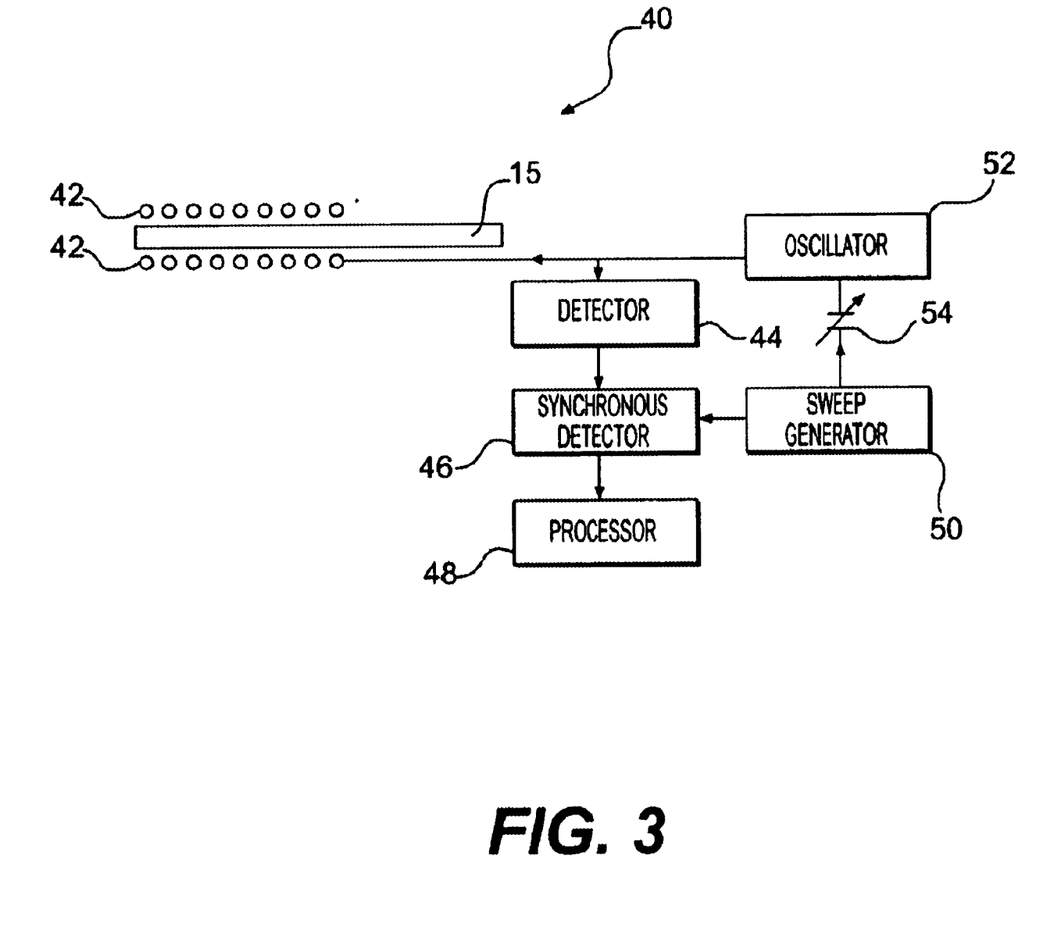
FIG. 3 a schematic view of an NQR spectrometer that is suitable for identifying or authenticating articles according to the present invention.

Another embodiment of a suitable apparatus for use in determining isotopic abundances is depicted in FIG. 3. An NQR spectrometer 40 operating in a pulse mode suitable to be used as a detection apparatus in the method of the present invention is illustrated in FIG. 3. One or more resonating coils 42 are located near article 15 to be tested. Article 15 is placed in the spectrometer 40 as shown. Oscillator 52 sends a signal and/or pulse to resonating coil 42, which then excites the nuclei of the isotopes of the labeling composition in article 15 and causes the nuclei to resonate. After the signal and/or pulse, the nuclei continue to resonate, which is detected by resonating coil 42 and sent to a detector 44. The output from detector 44 is then sent to synchronous detector 46. This process of excitation and resonation of the nuclei is controlled by a sweep generator 50, which controls synchronous detector 46 and also controls oscillator 52 via a frequency varying device 54. Synchronous detector 46 measures the isotope abundances and/or abundance ratio(s) in the labeling composition and optionally determines if the measured result is consistent with a predetermined labeling composition for a genuine article. The result of the determination is sent to a processor 48 to provide information about the article. In order to optimize the NQR spectrometer 40, a number of factors, such as T1 and T2 of the isotopes, number of isotope nuclei per unit volume and uniformity, the drive electronics and its pulse sequence and amplitude, the data acquisition time and processing, the coil configuration and sample handling arrangement, the robustness or error rate of the accept-reject decision process, and cost of production machines, etc, have to be considered.

In this embodiment, the NQR spectrometer 40 is operated in a pulse mode to detect the abundances and/or abundance ratio(s) of the isotopes used in the isotope labeling composition of the present invention. The resonating coil 42 applies a strong pulse at the resonant frequency of the isotope nuclei for a short time interval. Then as soon as the pulse ends, a sensitive detector 44 is turned on to observe the decay of the resonance of the nuclei through the resonating coil 42. This pulse method has many elaborations and is capable of measuring many of the nuclei properties in addition to the simple detection of isotope abundances and/or abundance ratio(s). In addition, the pulse method allows parameters to be adjusted for maximum sensitivity when the nuclear properties are known. The pulse and receive sequence typically takes less than a millisecond. To achieve high sensitivity it is usual to average the results of many pulse sequences, thus averaging out the noise and allowing the signal to build up.

In another embodiment, the NQR spectrometer 40 can be operated in a marginal oscillator mode that measures the nuclei quadrupole resonance of isotopes to detect the isotope abundances or abundance ratio(s) of the composition of the present invention. When NQR spectrometer 40 is used as a marginal oscillator, the resonating coil 42 emits a signal with a varied frequency (a signal with a sweeping frequency) instead of a pulse. When the frequency of the signal is swept past the NQR resonant frequency of the isotopes, the signal causes the nuclei of the isotopes to resonate and the NQR resonance of the isotopes absorbs some power from the oscillator 52 and hence decreases the amplitude of the oscillation to result in an output signal.

In a third embodiment, the NQR spectrometer 40 may also be operated in a superregenerative detector mode. In this embodiment, the circuit in oscillator 52 is so arranged that the oscillation signal generated by oscillator 52 starts and stops many times each second, e.g., 50,000 times per second. The circuit of the oscillator is arranged so that the oscillator 52 is turned "ON" only by changing the gain to where it is sufficient to oscillate. No starting impulse is supplied to the oscillator so the oscillations actually grow from the thermal agitation noise in the circuit components. If there is a signal present during this starting interval stronger than the thermal noise, then the oscillations grow quicker and result in an output signal. When used for NQR detection, the nuclei are resonantly excited during the oscillating period and when the oscillations turn off the nuclei continue to resonate and hence induce a signal during the next start up interval causing quicker growth and an output signal.

Figure 11:
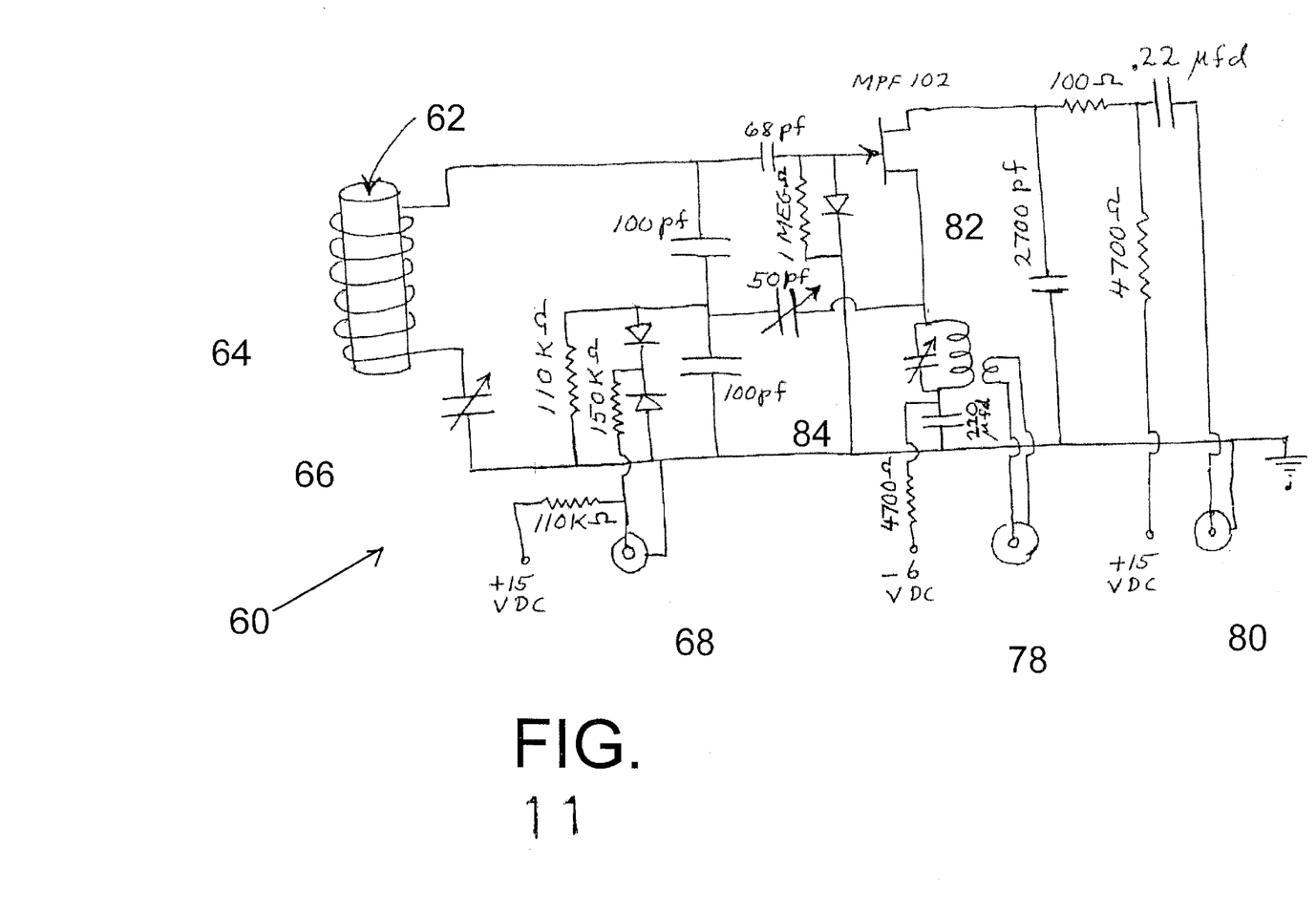
FIG. 11 schematically illustrates the configuration and circuit of an NQR spectrometer which can be used in detecting abundances and/or abundance ratios according to the invention.

The circuits for the NQR spectrometer 40 to be operated in the marginal oscillator and the superregenerative detector modes may be similar and often small changes can be made that change the mode of operation from one to the other. In addition, when the NQR spectrometer 40 is operated in the marginal oscillator and the superregenerative detector modes, not all of the components shown in FIG. 3 are necessary. An exemplary configuration and circuitry for another NQR spectrometer 60 operating in a marginal oscillator mode that can be used to detect isotope abundances and/or abundance ratios is illustrated in FIG. 11. NQR spectrometer 60 is used in detecting abundances and/or abundance ratios of chlorine-35 and chlorine-37 in the following example. In FIG. 11, a testing sample 62 is placed within an excitation coil 64. The frequency of excitation coil 62 is adjusted by a main frequency tuning device 66. NQR spectrometer 60 further includes a sweep voltage input 68, a feedback circuit 84, a phase adjustment circuit 82, an RF monitor 78 and an audio output 80. When the NQR spectrometer 60 in FIG. 11 is operated in a superregenerative detector mode, a small change is made to allow an external oscillator at 10 KHZ to turn the RF oscillations on and off.

Generally, to determine if a particular article is authentic or genuine, or to determine the information associating with the particular article, the article is subjected to isotope abundance and/or abundance ratio measurement using one of the methods described above. If the isotope abundances and/or isotope abundance ratios fall within a predetermined range or are equal to a predetermined value, then the article is considered to be authentic or genuine. Otherwise, the article may be considered counterfeit or non-authentic.

The invention will be further illustrated by the following non-limiting example.

EXAMPLE

Detection of Isotopes Using an NQR Spectrometer

An NQR spectrometer was built according to the configuration and circuitry illustrated in FIG. 11. For this example, the NQR spectrometer was operated in a marginal oscillator mode. However, this NQR spectrometer can be operated in a superregenerative mode with a minor adjustment. The material to be detected in this example was paradichlorobenzene ($C_6H_4Cl_2$). In the experiment, 150 grams of paradichlorobenzene in a bottle was kept at the center of a 12 inch cubic box of the NQR spectrometer. The bottle was surrounded by the main resonating coil of the spectrometer. The interior of the box was lined with copper foil to shield out any potential radio frequency interference. In addition, the spectrometer further included a magnetic field generating coil that generated a magnetic field of about 10 gauss at the location of the paradichlorobenzene being detected when a current passing through the magnetic field coil was turned on. Generally, the current supply to this magnetic field generating coil was turned on and off by a 6 Hz square wave. When the current was on, the 10 gauss magnetic field squashed out the resonance so that the resonating coil would not be able to detect the NQR. Accordingly, in one embodiment, the net output signal of the NQR spectrometer was, therefore, the difference between an output signal detected by the resonating coil with the current supply to the magnetic field generating coil turned off (therefore, zero field NQR active), and an output signal detected by the resonating coil with the current supply turned on (therefore, no NQR detected). In one case, the measurement of the output signal of the spectrometer could be carried out with the 6 Hz square wave current to the magnetic field generating coil being used. The output signal of the spectrometer was monitored by an oscilloscope connected to the audio output 80 shown in FIG. 11.

Figure 4:
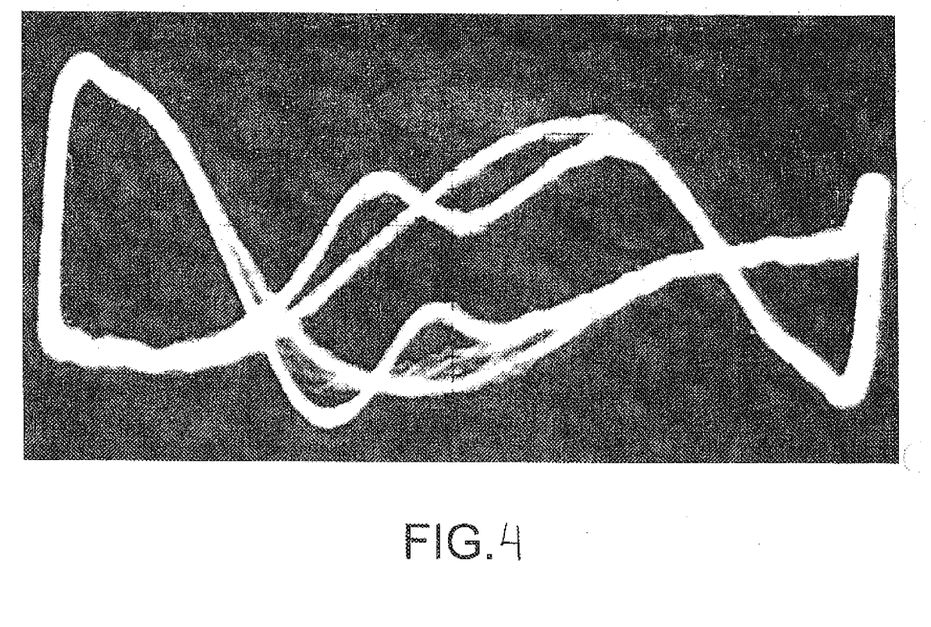
FIG. 4 is a signal output result of an NQR spectrometer in detecting chlorine-35 operating in a marginal oscillator mode according to one embodiment of the invention.

The measurement results with and without use of the 6 Hz square wave current are shown in FIG. 4. The results were a contorted lissajou plot with the horizontal sinusoidally sweeping back and forth at 60 Hz. The vertical axis of the plot represented the output from the spectrometer. The same 60 Hz voltage that drove the horizontal axis on the oscilloscope also swept the frequency of the spectrometer back and forth. Accordingly, the horizontal axis of the plot also represented the spectrometer frequency. Near the center of the plot in FIG. 4, where the trace was double, was the NQR output signal as the NQR spectrometer frequency operating in a marginal oscillator mode passed through the nuclear quadrupole resonance of the chlorine-35 isotope. The smoother trace of the plot was the NQR output signal detected by the resonating signal when the 6 Hz magnetic field produced by the magnetic field generating coil controlled by the 6 Hz square wave current was turned on to eliminate the NQR. The zig-zag trace of the plot was the NQR output signal detected by the resonating coil when the 6 Hz magnetic field was turned off. The isotope abundance of a particular isotope could be correlated with the strength of the NQR output signal. One can also infer from FIG. 4 that a detection time in milliseconds to detect abundances and/or abundance ratio of isotopes, is realistic.

Figure 5:
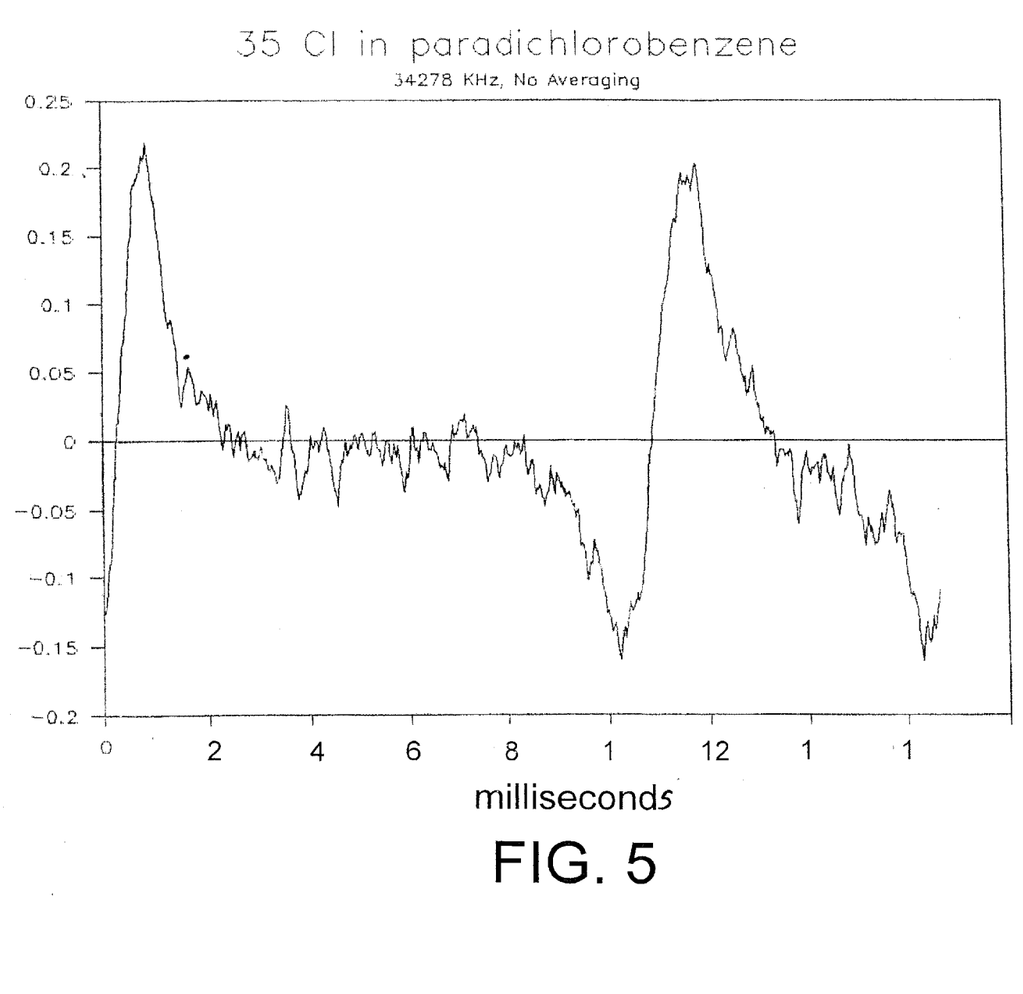
FIG. 5 is another signal output result in a computer printout format of an NQR spectrometer in detecting chlorine-35 according to one embodiment of the invention.

FIG. 5 is a computer printout of the chlorine-35 resonance observed by the NQR spectrometer operating in a marginal oscillator mode. This figure was produced by connecting the output of the NQR spectrometer to an A/D input of a computer. The horizontal axis of the plot in FIG. 5 again represented a frequency sweep of the NQR spectrometer. In this particular figure, the frequency swept up for the first half, and down for the second half of the plot trace in FIG. 5. The time for a full sweep was $\frac{1}{60}^{th}$ of a second. Actually the sweeps were done in pairs, one with no magnetic field and the other with the 10 gauss magnetic field. The vertical axis of FIG. 5 represented the difference between the two sweeps and thus represented the difference between the two traces of the plot shown in FIG. 4, the difference being the true NQR output signal without extraneous instrumentation artifacts.

Figure 6:
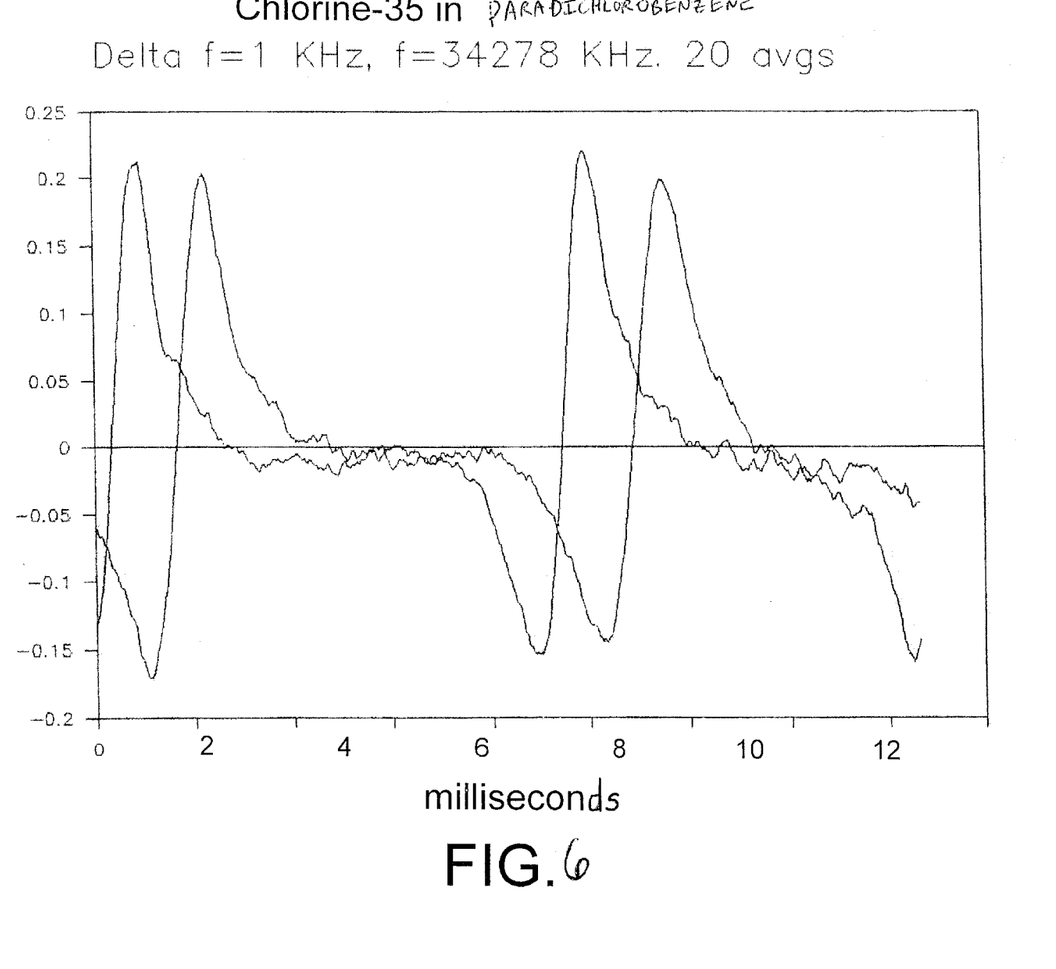
FIG. 6 is a signal output result, which is based on an average of 20 pairs of sweeps of an NQR spectrometer in detecting chlorine-35 according to one embodiment of the invention.

FIG. 6 is similar to FIG. 5 except that 20 pairs of sweeps have been carried out by the NQR spectrometer and the plot in FIG. 6 was the average of these 20 pairs. The noise of the averaged output was clearly reduced. In addition, a second run in which the NQR spectrometer frequency was offset by exactly 1 KHz was also plotted in FIG. 6. This offset of 1 KHz was comparable with the NQR output signal width and showed that the NQR output signal line width of this material was about 1 KHz.

Figure 7:
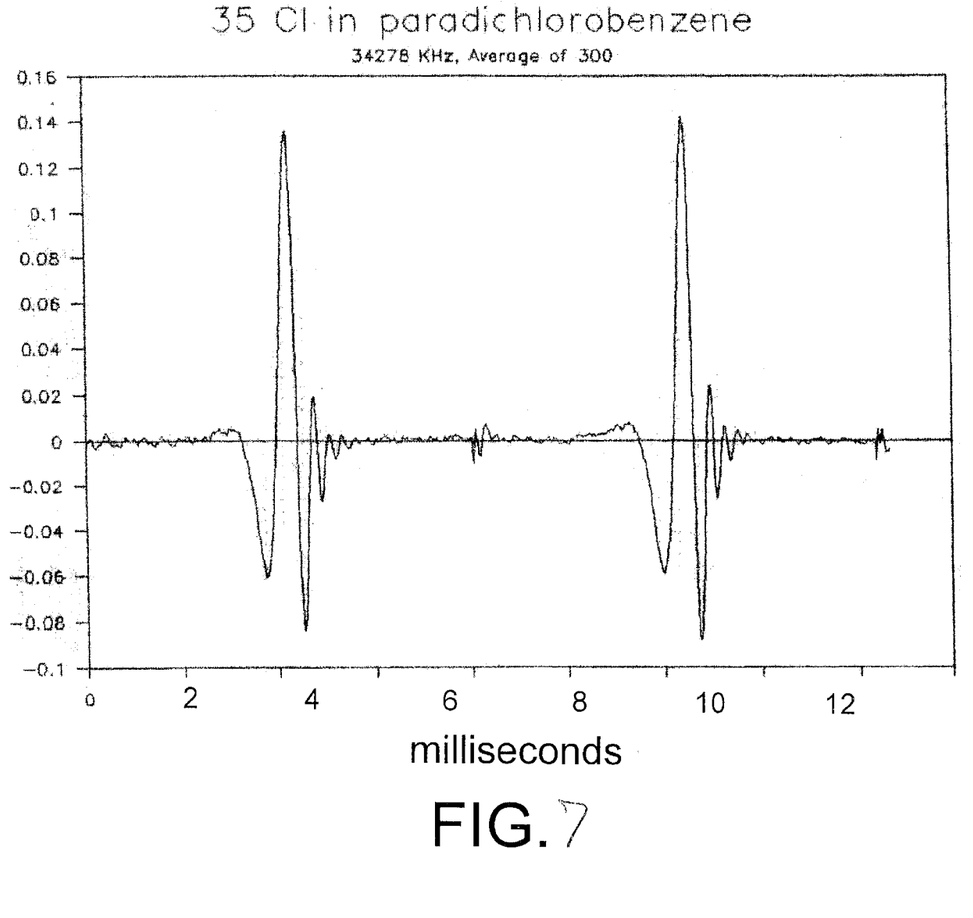
FIG. 7 is a signal output result, which is based on an average of 300 pairs of sweeps of an NQR spectrometer in detecting chlorine-35 according to one embodiment of the invention.

FIG. 7 is similar to FIGS. 5 and 6 except that 300 pairs of sweeps have been averaged in the plot of FIG. 7 and the NQR spectrometer parameters have been slightly changed to maximize the visibility of a phenomena referred to in the literature as "wiggles." Here one observed that as the NQR spectrometer frequency moved from left to right, that the NQR was excited and then as the NQR spectrometer frequency moved past the NQR frequency of chlorine-35, the NQR spectrometer oscillator beats with the decaying resonance of the chlorine-35 nuclei, going in and out of phase for several cycles. From the plot of FIG. 7, one could see that the NQR output signal, when the sweep was rapid, departed from the simple loading model (when the sweep was slow) shown in FIGS. 4–6.

Figure 8:
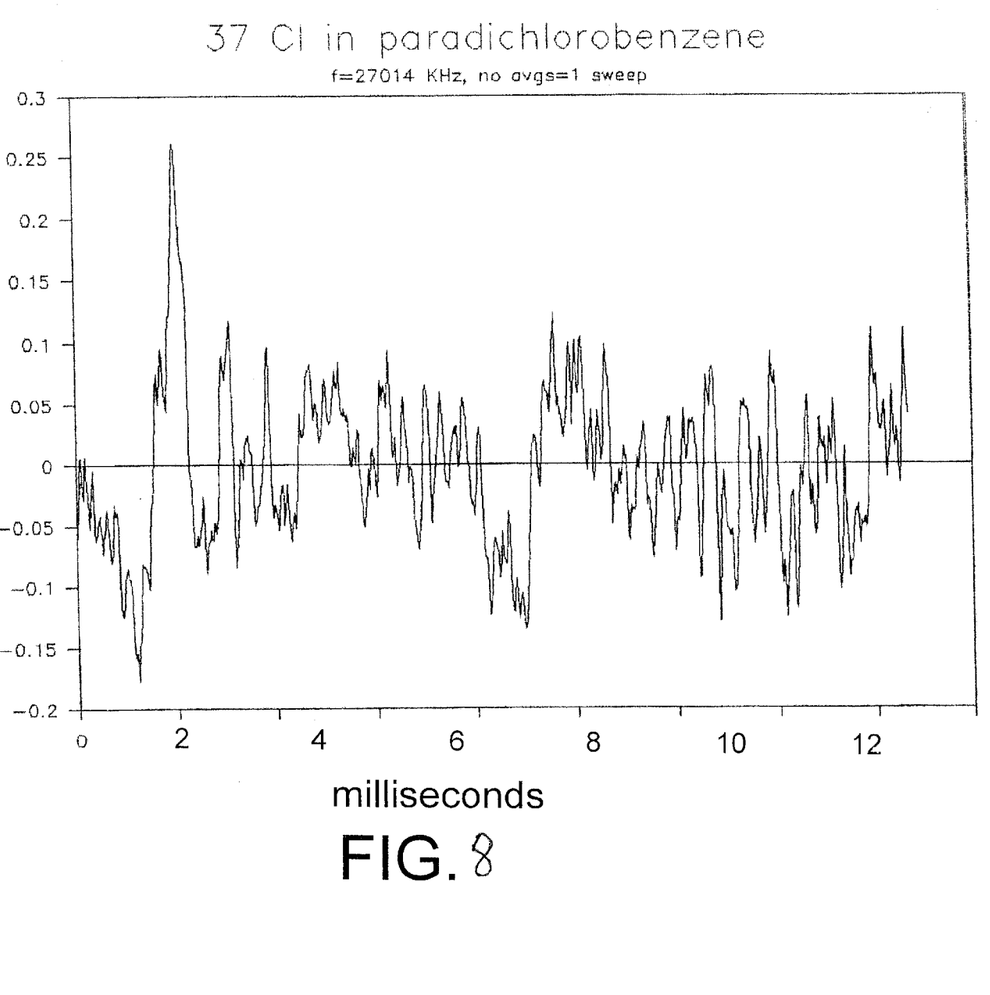
FIG. 8 is a signal output result of an NQR spectrometer in detecting chlorine-37 according to one embodiment of the invention.
Figure 9:
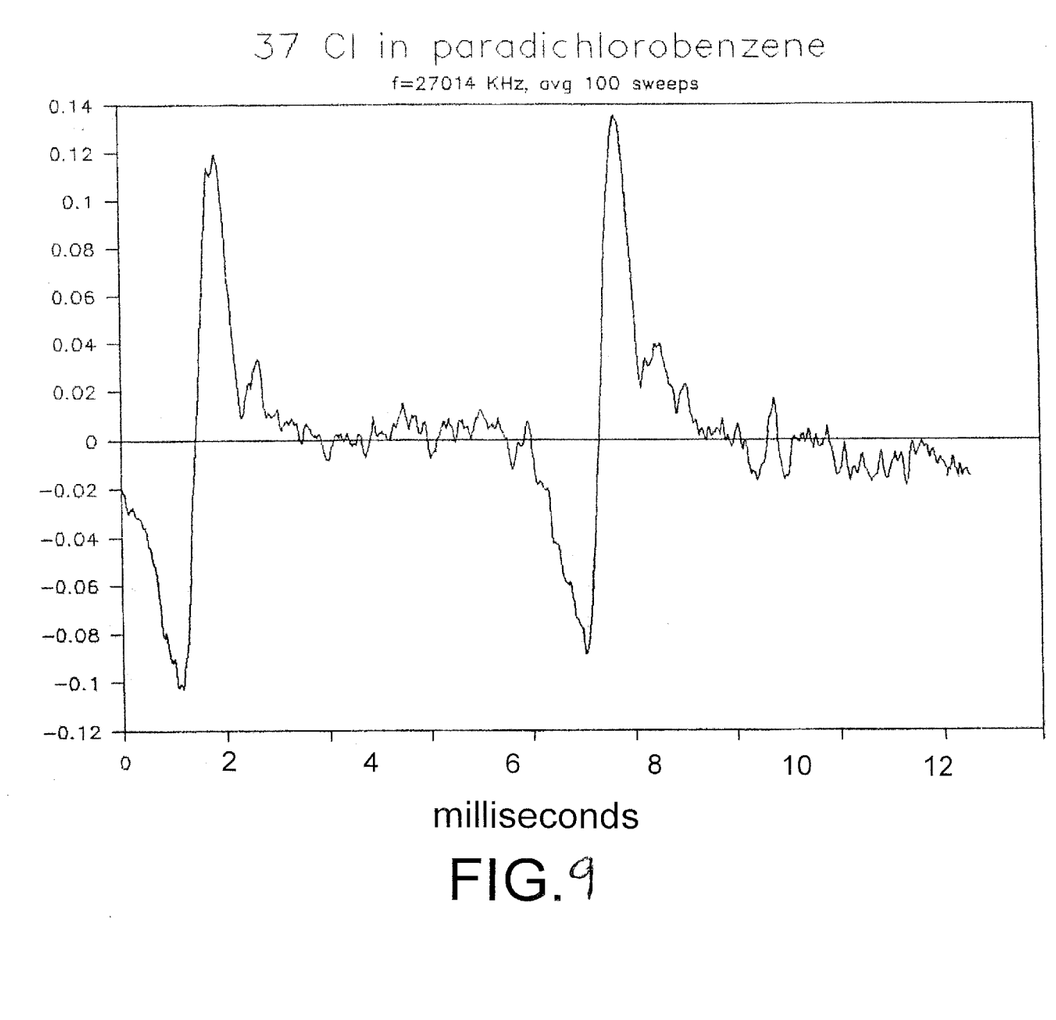
FIG. 9 is a signal output result, which is based on an average of 100 pairs of sweeps of an NQR spectrometer in detecting chlorine 37 according to one embodiment of the invention.
Figure 10:
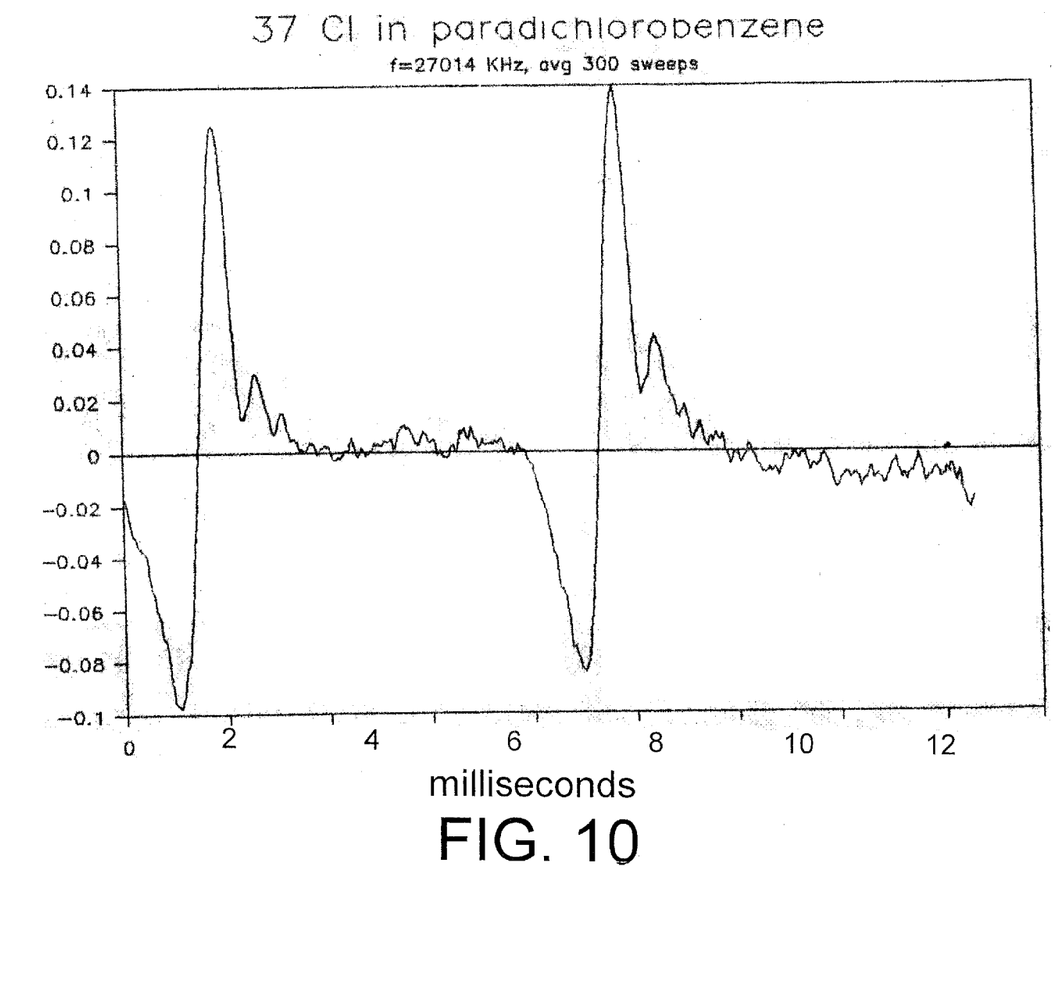
FIG. 10 is a signal output result, which is based on an average of 300 pairs of sweeps of an NQR spectrometer in detecting chlorine-37 according to one embodiment of the invention.

FIGS. 8–10 are the corresponding figures to FIGS. 5–7 for measuring the NQR output signals of the other chlorine isotope, chlorine-37. Generally, the signals from chlorine-37 were about six times smaller than the signals from chlorine-35 for this particular sample, whose isotope abundance ratio was equal to the natural abundance ratio, because the natural abundance of chlorine-37 is about one third of chlorine-35. In addition the NQR frequency of chlorine-37 is lower and the magnetic moment of the nucleus of chlorine-37 is also smaller in comparison with those of chlorine-35. Accordingly, the signal for chlorine-37 in FIG. 8 was weaker than the corresponding signal of chlorine-35 in FIG. 5.

From this example, it is apparent that if the same instrumentation were applied to a sample in which the ratio of chlorine-37 to chlorine-35 had been enriched by a factor of six relative to the natural abundance ratio, the two isotopes would then give comparable output signals and the enriched ratio material would be readily distinguished from the material containing the chlorine isotopes in their natural abundance.

It will be apparent to a skilled person that certain changes may be made in carrying out the above method and in the compositions and articles set forth without departing from the spirit and scope of the invention, it is intended that all matter contained in the above description and shown in the accompanying drawing shall be interpreted as illustrative and not in a limiting sense. The scope of the invention is to be determined from the claims appended hereto.

What is claimed is:

1. A method to associate information with an article comprising the steps of:
    labeling said article with a composition comprising at least two different isotopes of an element, wherein an abundance ratio between said at least two isotopes is different from the natural abundance ratio between said at least two isotopes, and wherein said isotopes are resonant materials that resonate detectably different responses;
    detecting the abundance each of said isotopes using a detection method selected from the group consisting of nuclear quadrupole resonance spectroscopy, nuclear magnetic resonance spectroscopy, laser ablation/ magnetic spectroscopy, infrared spectroscopy and microwave spectroscopy, by measurement of the resonance responses of said at least two iostopes;
    determining the abundance ratio of said at least two iostopes using the measured resonance responses; and
    determining information about said article from the determined abundance ratio of said at least two iostopes.

2. A method as claimed in claim 1, wherein said element is selected from the group consisting of rhenium, copper, rubidium, antimony, tin, europium and indium.

3. A method as claimed in claim 2, wherein said isotopes are in elemental form.

4. A method as claimed in claim 1, wherein said labeling step is accomplished by a method selected from the group consisting of embedding said composition into said article, adhering said composition to a surface of said article, and mixing said composition with said article.

5. A method as claimed in claim 1, wherein said detection method is nuclear quadrupole resonance.

6. A method as claimed in claim 5, wherein said element is selected from the group consisting of copper and antimony.

7. A method as claimed in claim 1, wherein said detection method is nuclear magnetic resonance.

8. A method as claimed in claim 7, wherein said element is selected from the group consisting of tin, antimony, and indium.

9. A method as claimed in claim 7, wherein said composition comprising at least two iostopes is dissolved or dispersed in a carrier that permits micro-structural mobility of said composition in said carrier.

10. A method as claimed in claim 9, wherein in said labeling step said composition is dissolved or dispersed in a carrier selected from the group consisting of plastics, rubbers, oil, wax, solvents, water, alcohol and mixtures thereof, and wherein said carrier permits determination of the abundance of each of said at least two isotopes when dissolved or dispersed in said carrier.

11. A method as claimed in claim 1, wherein said element is in a form of a compound containing said element.

12. A method as claimed in claim 11, wherein said compound is selected from the group consisting of $ReBr_3$, $ReO_2$, $ReS_2$, $CuF_2$, $Cu(NO_3)_2,3H_2O$, $CuO$, $Cu_2O$, $Cu_2S$, $CuS$, $Rb_2CO_3$, $RbF$, $RbNO_3$, $Rb_2SO_4$, $Sb_2O_5$, $Sb_2O_3$, $SbCl_3$, $SbF_3$, $Eu_2O_3$, $EuCl_3$, $EuF_3$, $EuBr_3$, $InF_3$, $InCl_3$, $InBr_3$, $C_6H_4Cl_2$, and $C_6H_4Br_2$.

13. A method as claimed in claim 1, wherein said element is in a form selected from the group consisting of: an alloy, a powdered metal and a eutectic.

14. A method as claimed in claim 13, wherein said element is selected from the group consisting of tin, antimony, copper and indium.

15. An isotopic labeling composition, which comprises at least two isotopes of an element at a predetermined abundance ratio between said at least two isotopes, wherein said predetermined abundance ratio is detectably different from the natural abundance ratio between said at least two isotopes, and said isotopes are resonant materials that resonate detectably different responses.

16. A labeling composition as claimed in claim 15, wherein said element is selected from the group consisting of rhenium, copper, rubidium, antimony, tin, europium and indium.

17. A labeling composition as claimed in claim 16, wherein said isotopes are in elemental form.

18. A labeling composition as claimed in claim 15, wherein said element is selected from the group consisting of copper and antimony.

19. A labeling composition as claimed in claim 15, wherein said element is selected from the group consisting of tin, indium and antimony.

20. A labeling composition as claimed in claim 19, further comprising a carrier.

21. A labeling composition as claimed in claim 20, wherein said carrier is selected from the group consisting of plastics, rubbers, oil, wax, solvents, water, alcohol and mixtures thereof.

22. A labeling composition as claimed in claim 21, wherein said carrier is a rubber.

23. A labeling composition as claimed in claim 21, wherein said carrier is a liquid in which said isotopic labeling composition is soluble or partially soluble.

24. A labeling composition as claimed in claim 21, wherein said carrier permits micro-structural mobility of a composition containing said element in said carrier.

25. A labeling composition as claimed in claim 15, wherein said element is in a form of a compound containing said element.

26. A labeling composition as claimed in claim 25, wherein said compound is selected from the group consisting of $ReBr_3$, $ReO_2$, $ReS_2$, $CuF_2$, $Cu(NO_3)_2,3H_2O$, $CuO$, $Cu_2O$, $Cu_2S$, $CuS$, $Rb_2CO_3$, $RbF$, $RbNO_3$, $Rb_2SO_4$, $Sb_2O_5$, $Sb_2O_3$, $SbCl_3$, $SbF_3$, $Eu_2O_3$, $EuCl_3$, $EuF_3$, $EuBr_3$, $InF_3$, $InCl_3$, $InBr_3$, $C_6H_4Cl_2$, and $C_6H_4Br_2$.

27. A labeling composition as claimed in claim 15, wherein said element is in a form selected from the group consisting of: an alloy, a powdered metal and a eutectic.

28. A labeling composition as claimed in claim 27, wherein said element is selected from the group consisting of tin, antimony, indium and copper.

29. An article of manufacture which comprises an isotope labeling composition, wherein said isotope labeling composition comprises at least two different isotopes of an element at a first predetermined abundance ratio that is detectably different from the natural abundance ratio between said at least two isotopes, and said isotopes are resonant materials that resonate detectably different responses.

30. An article claimed as claim 29, wherein said element is selected from the group consisting of rhenium, copper, rubidium, antimony, tin, europium and indium.

31. An article claimed as claim 29, wherein said article is selected from the group consisting of currency, luxury goods, designer goods, charge cards, debit cards, identification documents, passports, licenses, negotiable instruments, tickets, collector's items, precious metals, jewels, rare goods, ingestible products, stock certificates, and medical devices.

32. An article as claimed in claim 31, wherein said isotopic labeling composition is distributed on said article in a first predetermined pattern to thereby provide additional information about said article from said first isotopic labeling composition.

33. An article as claimed in claim 29, further comprising a second isotopic labeling composition, wherein said second isotopic labeling composition comprises at least two different isotopes of a second element at a predetermined abundance ratio that is detectably different from the natural abundance ratio between said at least two isotopes of said second isotopic labeling composition.

34. An article as claimed in claim 33, wherein said elements are in a form selected from the group consisting of: an alloy, a powdered metal and a eutectic.

35. An article as claimed in claim 29, further comprising a second isotopic labeling composition, wherein said second isotopic labeling composition comprises at least two different isotopes of said element at a second predetermined abundance ratio that is detectably different from the first predetermined abundance ratio.

36. An article as claimed in claim 29, wherein said isotopic labeling composition comprises at least three different isotopes of an element at predetermined abundance ratios that are detectably different from the corresponding natural abundance ratios among said at least three isotopes.

37. An article as claimed in claim 29, wherein said isotopic labeling composition comprises at least four different isotopes of an element at predetermined abundance ratios that are detectably different from the corresponding natural abundance ratios among said at least four isotopes.

* * * * *